(12) United States Patent
Kenning

(10) Patent No.: US 9,041,419 B2
(45) Date of Patent: May 26, 2015

(54) THERMALLY ACTIVATED MAGNETIC AND RESISTIVE AGING

(75) Inventor: Gregory G. Kenning, Indiana, PA (US)

(73) Assignee: Indiana University of Pennsylvania, Indiana, PA (US)

( * ) Notice: Subject to any disclaimer, the term of this patent is extended or adjusted under 35 U.S.C. 154(b) by 190 days.

(21) Appl. No.: 13/446,579

(22) Filed: Apr. 13, 2012

(65) Prior Publication Data

US 2012/0262194 A1    Oct. 18, 2012

Related U.S. Application Data

(60) Provisional application No. 61/476,044, filed on Apr. 15, 2011.

(51) Int. Cl.
| | | |
|---|---|---|
| G01N 27/04 | (2006.01) | |
| G01R 27/08 | (2006.01) | |
| B82Y 40/00 | (2011.01) | |
| B82Y 30/00 | (2011.01) | |

(52) U.S. Cl.
CPC ...... *B82Y 40/00* (2013.01); *B82Y 30/00* (2013.01)

(58) Field of Classification Search
CPC ........ G01R 33/14; G01R 33/16; G01R 27/08; G01R 27/27; G01R 27/22; G01R 31/06; G01N 27/00; G01N 27/04; G01N 27/06
USPC ........ 324/693, 201, 223, 71.1, 545–547, 649, 324/750.3, 601, 655, 663, 684, 705, 715, 324/654, 691, 541, 543; 257/7; 422/90, 422/82.02, 82.01, 68.1, 83, 88, 98, 50; 250/221, 222.2
See application file for complete search history.

(56) References Cited

U.S. PATENT DOCUMENTS

| | | | |
|---|---|---|---|
| 4,949,039 A | 8/1990 | Grunberg | |
| 5,057,434 A | 10/1991 | Prusik et al. | |
| 5,064,605 A | 11/1991 | Ruddy et al. | |
| 5,201,583 A | 4/1993 | Lai et al. | |
| 5,932,813 A | 8/1999 | Swartzel et al. | |
| 5,975,758 A * | 11/1999 | Yokota et al. | 374/185 |
| 6,617,963 B1 | 9/2003 | Watters et al. | |

(Continued)

FOREIGN PATENT DOCUMENTS

EP    0443260 A1    8/1991

OTHER PUBLICATIONS

G.G. Kenning, J. Bowen, P. Sibani, G.F. Rodriguez, "Temperature Dependence of Fluctuation Time Scales in Spin Glasses," Phys. Rev. B, 2010.

(Continued)

*Primary Examiner* — Arleen M Vazquez
*Assistant Examiner* — Neel Shah
(74) *Attorney, Agent, or Firm* — Gifford, Krass, Sprinkle, Anderson & Citkowski, P.C.

(57) ABSTRACT

Examples of the present invention include apparatus and methods for monitoring aging of an item. A solid-state structure is located within, adjacent to, or otherwise proximate the item, the solid-state structure including nanostructures. The electrical resistance and/or magnetization of the solid-state structure is determined to determine the degree of aging of the item. In representative examples, the solid-state structure includes nanostructures of a metal, such as a ferromagnetic metal, within a non-magnetic matrix, such as a semimetal, semiconductor, or insulator.

20 Claims, 11 Drawing Sheets

(56) References Cited

U.S. PATENT DOCUMENTS

| | | | |
|---|---|---|---|
| 6,642,016 B1 | 11/2003 | Shoholm et al. | |
| 7,537,384 B2 | 5/2009 | Hilgers | |
| 7,592,277 B2* | 9/2009 | Andrady et al. | 442/340 |
| 7,612,325 B1 | 11/2009 | Watkins, Jr. et al. | |
| 7,697,243 B1* | 4/2010 | Novosad et al. | 360/324 |
| 7,719,404 B2* | 5/2010 | Makela et al. | 338/200 |
| 7,898,833 B2 | 3/2011 | Prejbeanu et al. | |
| 8,177,423 B1* | 5/2012 | Fair et al. | 374/44 |
| 8,217,669 B1 | 7/2012 | Watkins, Jr. | 324/693 |
| 8,253,124 B2* | 8/2012 | Numata et al. | 257/9 |
| 8,343,437 B2* | 1/2013 | Patel | 422/424 |
| 8,443,647 B1* | 5/2013 | Kolmakov et al. | 73/1.02 |
| 2005/0061496 A1* | 3/2005 | Matabayas, Jr. | 165/185 |
| 2005/0093556 A1* | 5/2005 | Mueller et al. | 324/693 |
| 2007/0166831 A1 | 7/2007 | Watkins et al. | |
| 2007/0176773 A1* | 8/2007 | Smolander et al. | 340/539.26 |
| 2008/0150556 A1* | 6/2008 | Han et al. | 324/693 |
| 2009/0087348 A1 | 4/2009 | Claus et al. | |
| 2009/0165533 A1* | 7/2009 | Han et al. | 73/31.06 |
| 2009/0301382 A1* | 12/2009 | Patel | 116/201 |
| 2010/0068749 A1 | 3/2010 | Bauer et al. | |
| 2010/0109645 A1 | 5/2010 | Park et al. | |
| 2010/0191474 A1* | 7/2010 | Haick | 702/19 |
| 2010/0296545 A1 | 11/2010 | Haarer et al. | |
| 2011/0003279 A1* | 1/2011 | Patel | 435/5 |
| 2011/0038395 A1 | 2/2011 | Sorkine et al. | |

OTHER PUBLICATIONS

H. Park, M. Pleimling, "Aging in coarsening diluted ferromagnets," *Phys. Rev. B*82, 144406 (2010).

P.R. Rios, F. Siciliano Jr., H.R. Zschommler Sandim, R.L. Plaut, A.F. Padilha, "Nucleation and Growth During Recrystallization," *Materials Research*, vol. 8, No. 3, 225-238, 2005.

M. Sachan, C. Bonnoit, S.A. Majetich, Y. Ijiri, P.O. Mensah-Bonsu, J.A. Borchers, and J.J. Rhyne, "Field evolution of magnetic correlation lengths in ∈-Co nanoparticle assemblies," *Applied Physics Letters* 92, 152503 (2008).

Y. Jun, J. Seo, J. Cheon, "Nanoscaling Laws of Magnetic Nanoparticles and Their Applicabilities in Biomedical Sciences," *Accounts of Chemical Research*, vol. 41, No. 2, 179-189, Feb. 2008.

Supplementary European Search Report from co-pending application Serial No. EP12770711, issued Aug. 13, 2014.

\* cited by examiner

FIG. 9A
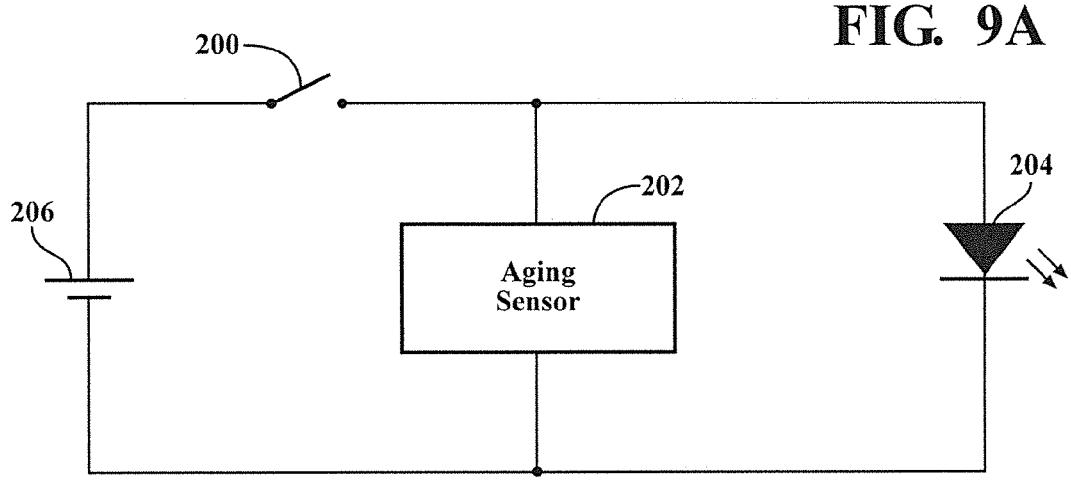
FIG. 9B
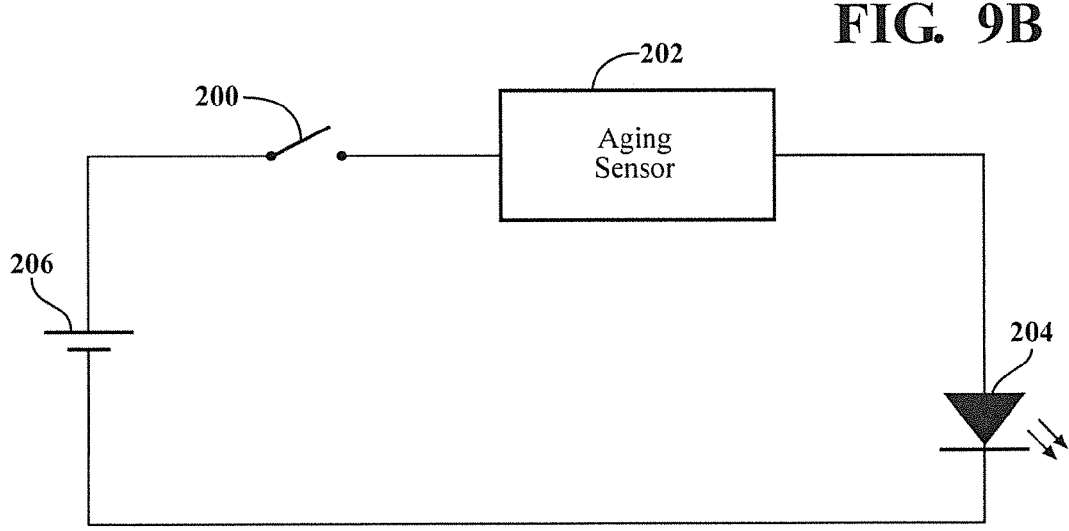
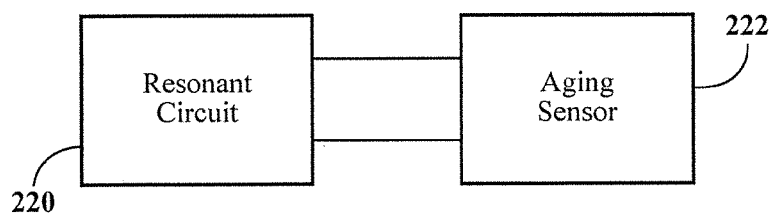
FIG. 9C

THERMALLY ACTIVATED MAGNETIC AND RESISTIVE AGING

CROSS-REFERENCE TO RELATED APPLICATIONS

This application claims priority from U.S. Provisional Application 61/476,044 filed Apr. 15, 2011, the contents of which are incorporated herein by reference.

FIELD OF THE INVENTION

Examples of the invention relate to methods and apparatus for monitoring aging processes, for example using a solid-state apparatus.

BACKGROUND OF THE INVENTION

Aging processes are significant in many commercial activities, including handling of perishable items such as food and medicine, part lifetimes in engineering applications, process control, and the like. A typical approach is to determine an end-of-life date as a fixed time period from the initial manufacture. However, this fails to account for variations in temperature or other ambient conditions during the lifetime.

Hence, there is a need for improved methods and apparatus allowing monitoring of aging processes in a variety of applications.

SUMMARY OF THE INVENTION

Examples of the present invention include apparatus and methods for monitoring aging, for example in a monitored item such as a physical system. An example apparatus includes a solid-state sensor material which has a physical property that varies as a function of both time and temperature. In examples, the physical property may be electrical resistance, magnetoresistance, or magnetization. An example may include a solid-state composite structure including nanoparticles of a first material, for example a ferromagnetic material such as a ferromagnetic metal. The nanoparticles may be spherical nanoparticles, nanorods, nanoflakes, and the like. The matrix material preferably has a physical property, such as electrical resistivity, appreciably different from the ferromagnetic material. In some examples, the solid-state structure may include alternating layers of a nanostructured material, such as a metal, and a matrix material.

Typically, the physical property changes faster with time as the temperature increases. Hence, aging properties of items can be evaluated in a more accurate manner than using a simple timing mechanism. For example, in some aspects, a solid-state structure used as an aging sensor has an electrical resistance (or resistivity) that changes as a function of both time and temperature, providing an indication of aging in an associated item.

In some examples, nanoparticles, such as nanoflakes, of a first material, such as a ferromagnetic material, are supported within a matrix, such as a semi-metal or semiconducting matrix. Preferably, the matrix material has an electrical conductivity significantly less than the nanoparticle material. In some examples, morphological changes occur within the sensor material, causing an appreciable change in electrical conductivity. Nanostructures may melt and interact with each other to form nanowires of the first material within the matrix material. The electrical conductivity falls appreciably as nanowire networks form through the matrix material, and this may be detected using a pair electrodes. Morphological changes may reduce the magnetization of the solid-state material, which can be detected using a GMR (giant magnetoresistance) sensor.

In some examples, the first material may be a metal, such as a ferromagnetic metal. The matrix material may be a metal, semimetal, semiconductor, or insulator. Morphological changes in nanostructures of the first material reduce the electrical resistance of the solid-state structure, due to at least partial melting of the first material and formation of nanowires of the first material, during aging.

The melting of nanostructures of the first material, such as ferromagnetic nanoflakes, and the formation of nanowires thereof may result from an interaction between the nanoparticles, and this may be facilitated by magnetic interactions between proximate ferromagnetic nanostructures, such as nanoparticles.

A method of monitoring aging of an item comprises locating a solid-state structure proximate the item, for example adjacent the item, within or on the item packaging, or otherwise located so that the sensor and the item experience similar or correlated temperatures as a function of time. For example, an aging sensor may be placed on a food package, on a supporting shelf, or in the same room.

An example aging sensor includes a solid-state structure having nanostructures of a first material, such as a ferromagnetic material, distributed in a non-ferromagnetic matrix material. A physical parameter of the solid-state structure (such as electrical resistance, magnetization, or in some cases magnetoresistance) is determined at intervals. The physical parameter varies with both time and temperature of the solid-state structure, allowing the effects of both to be used to determine when aging has reached a threshold level (for example, related to food spoilage, chemical process completion, or other desirable or undesirable aging process).

A physical parameter is determined relative to an initial value of the physical parameter, for example as a ratio of the current value physical parameter and the initial value, and used to determine the aging of the item. Hence, advantageously, both time and temperature variations are used in the determination of aging.

In some examples, physical parameter varies due to morphological changes of the nanostructures within the solid-state structure, such as melting of nanostructures such as ferromagnetic nanoflakes. In some examples, nanoflakes of cobalt, iron, manganese, nickel, or a ferromagnetic rare earth metal are formed within a semimetal matrix, including arsenic, antimony, tin, or bismuth, alloys thereof, or other semimetallic material. In some examples, the matrix material may be a semiconductor, such as a semiconducting polymer.

In some examples, electrical resistance decreases as the item ages, and this decrease may be determined using an electronic circuit, either combined with the solid-state structure in a unitary device, or as a separate circuit that can be electrically connected to the aging sensor. For example, electrical resistance changes may be detected by an electronic circuit. In some examples, an electronic circuit including a GMR sensor may be used to monitor changes in magnetization of the solid-state structure.

An alert, such as a visual or audible alert, may be provided if aging has reached a predetermined threshold. A monitored item may be food item, medical item, chemical compound such as pharmaceutical or industrial process chemical, reaction vessel, other chemical or biological process, or a mechanical component.

An example apparatus for monitoring a degree of aging of an item includes a solid-state structure including nanostructures of a first material, such as a ferromagnetic material, distributed in a (non-ferromagnetic) matrix material, the solid-state structure having a physical parameter, the physical parameter being an electrical resistance or a magnetization, where the physical parameter decreases with time, and the rate of decrease increases with an increase in ambient temperature (within an operational temperature range, and during the useful lifetime of the device).

An example solid-state structure includes nanostructures of a first material, such as a ferromagnetic material, distributed through a non-ferromagnetic matrix material, may be enclosed in a housing. The non-ferromagnetic matrix material has an electrical resistivity appreciably greater than that of the ferromagnetic material, so that an electrical resistance measured between first and second electrodes, in electrical contact with the solid-state structure, falls as the morphology of the nanostructures changes, for example through the formation of nanowires of the first material.

In a representative process for forming a sensor, a matrix material (such as a metal, semi-metal, semiconductor, or dielectric matrix material) and first material (such as a ferromagnetic material) are alternately deposited on a substrate. The resulting structure may be termed a multilayer structure, however this may simplify the actual structure as discussed in more details later. For example, the first material may self-assemble into nanostructures. For example, a solid-state (nominally) multilayer structure may have the form substrate/ matrix layer/first material layer/matrix layer. The number of first material layers may be from, for example, 1 to 100 layers.

The first material may be ferromagnetic material, and may be a ferromagnetic metal such as cobalt, iron, manganese, alloys thereof, and the like. A preferred ferromagnetic metal is cobalt.

The matrix material preferably has an electrical conductivity appreciably less than the ferromagnet, and may for example be a semi-metal such as arsenic, antimony, bismuth, tin, and the like. In some examples, the matrix material may be a semiconductor. In some examples, the matrix material may be an insulating material such as a dielectric material.

In further examples, an array of ferromagnetic nanoparticles are supported within a matrix material, and magnetic interactions between neighboring nanoparticles result in temperature and time dependent magnetoresistance and magnetization. Changes in physical properties may be due to an electronic effect. An example device includes an array of ferromagnetic nanoparticles dispersed through a nonferromagnetic matrix. RKKY electronic interactions between proximate nanoparticles cause spin flipping of the ferromagnetic state and hence modifications in electrical conductivity. A magnetoresistance effect may be observed, and this effect may be reversible using a strong magnetic field to reset and reuse the aging sensor.

An improved method of fabricating an aging sensor includes depositing alternating layers of a first material and a matrix material on a substrate, the first material forming self-assembled nanostructures between matrix layers. The nanostructures in each layer of the solid-state structure formed then melt into each other during operation of the example aging sensor, providing an reduced electrical conductivity path through the structure.

Examples of the invention relate to monitoring a physical property (e.g. electrical resistance or magnetization) of a solid-state device to measure of the aging of an associated item (such as a physical or other system). Example devices include a magnetic multilayer structure, and structures including magnetic nanoparticles. Examples include solid-state structures, such as multilayer structures, that show aging properties as a function of time and temperature. Aging may be observed as appreciable changes in the magnetization and/or resistance of the device as a function of time.

A characteristic time can be associated with one or more decay processes, for example in magnetization and/or electrical resistance of the sensor material. An example sensor may be configured to operate as clock, or a switch that, at a particular time (dependent on the temperature), switches off or on. A multilayer structure can be configured to give a desired characteristic time, and characteristic times may be in the range of seconds, hours, days, weeks, or other desired range.

Monitored items may include food products (including beverages), chemicals such as pharmaceuticals, mechanical components, and the like.

BRIEF DESCRIPTION OF THE FIGURES

FIGS. 9A-9C illustrate possible electronic circuits including an aging sensor.

DETAILED DESCRIPTION OF THE INVENTION

Figure 1:
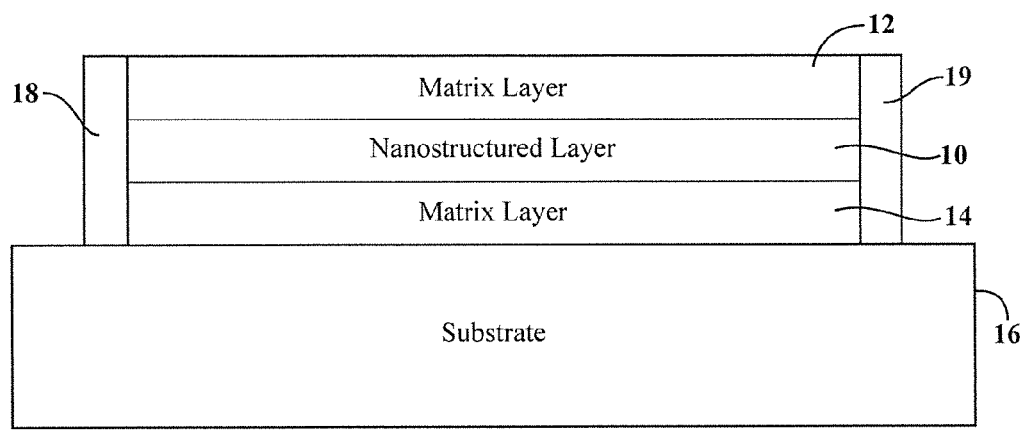
FIG. 1 is a simplified schematic of a multilayer sensor.

Examples of the present invention include apparatus and methods for monitoring aging in a monitored item (e.g. a physical system), using magnetic and/or resistive aging of a nanoparticle system. Examples include a solid-state structure including nanostructures of a first material distributed in a matrix material, in some examples as a multilayer structure including layers of nanostructures and layers of a matrix material. Some examples include ferromagnetic nanostructures (such as nanoparticles) within a semi-metal matrix material.

Appreciable magnetization (in particular, for ferromagnetic nanostructures) and electrical resistance decays may be observed, and a characteristic time determined. The characteristic time is strongly temperature dependent, so that the magnetization and resistance decrease as a function of both time and temperature. Further, the characteristic time may be controlled using deposition properties. Hence, the characteristic time can be predetermined to correlate with the aging processes in a monitored item.

Examples of the present invention include the use of magnetization and/or resistance aging decays in magnetic multilayer structures to characterize the aging of a system under test. Example magnetic multilayers include Co/Sb multilayer systems.

In experimental observations, aging was characterized by a large decay in both the magnetization (80% decay in some examples) and the resistivity (40% decay in some examples). A characteristic time can be assigned to the decay curves, for example as a point of inflection or as the time for a predetermined fall in the measured physical parameter.

In ferromagnetic/semimetal solid-state structures, resistivity did not require an applied magnetic field to decay and to first order is field independent. These data suggest that both the initial pre-aged is nominally super ferromagnetic and final post-aged samples are possibly super ferromagnetic. Analysis indicates aging is caused by thermally induced fluctuations in single domain Co nanoparticles and their interaction with the magnetic and electronic environment.

Examples of the present invention include an electronic device configured for aging monitoring. At a given temperature, this material acts like a clock and a switch. The accuracy of the clock is dependent on experimental variations in fluctuations in the $\tau_i$ timescale, which can be improved using modified techniques of nanoparticle deposition and characterization. This type of clock and switch might be useful in epidermal drug delivery or as a more accurate indicator of the age of perishable chemicals or foods, and the like.

Experimental time parameters were observed in timescales ranging from seconds to minutes to hours to days to weeks. The temperatures at which these timescales are observed ranged from just below room temperature all the way up to about 120° C. However, these observed values are not limiting.

Magnetic and resistive aging were observed in self-assembled nanoparticle systems produced in a multilayer Co/Sb sandwich. The aging decays are characterized by an initial slow decay followed by a more rapid decay in both the magnetization and resistance. The decays are large accounting for almost 70% of the magnetization and almost 40% of the resistance for samples deposited at 35° C. For samples deposited at 50° C. the magnetization decay accounts for ≈50% of the magnetization and 40% of the resistance During the more rapid part of the decay, the slope of the decay changes sign and this inflection point can be used to provide a characteristic time. The characteristic time is strongly and systematically temperature dependent, ranging from ≈100 s at 400K to ≈300,000 s at 320K in samples deposited at 35° C. Samples deposited at 50° C. displayed a 7-8 fold increase in the characteristic time (compared to the 35° C. samples) for a given aging temperature, indicating that this timescale is tunable. Both the temperature scale and time scales are in potentially useful regimes.

Pre-aging, scanning tunneling microscopy (STM) revealed that the Co forms in nanoscale flakes. During aging, the nanoflakes melt and migrate into each other in an anisotropic fashion forming elongated Co nanowires. This aging behavior occurs within a confined environment of the enveloping Sb layers. The relationship between the characteristic time and aging temperature fits an Arrhenius law indicating activated dynamics.

Examples of the present invention include methods and apparatus related to thermally activated magnetic and magnetoresistive aging, including applications at ambient temperatures and a wide variety of useful timescales. Producing this functionality in a solid-state device offers many advantages, including miniaturization, integration with electronic devices, reduced cost, and improved control. It is possible to quantitatively attach a value of the material property to a particular system age. A large change in a physical component such as the magnetization or in particular the resistance can be used as a switch. As a detectable change occurs at a given time for a particular temperature, applications include uses as a clock. At a given temperature, these material act like a clock which at a particular time effectively flips a switch.

The temperature dependence of the magnetic and electrical response provides an improved set of aging criteria, compared with a simple elapsed time. In this respect, the hotter the temperature, the faster the material ages, and the faster the switch is thrown. This is useful as a more accurate indicator of the age of chemicals, foods, etc., and allows improved expiration dates to be determined compared with approaches that stamp a date without product monitoring.

In representative examples, the time-dependent magnetization and resistivity of a Co/Sb multilayer were evaluated, as a function of deposition time and annealing time.

Figure 1A:
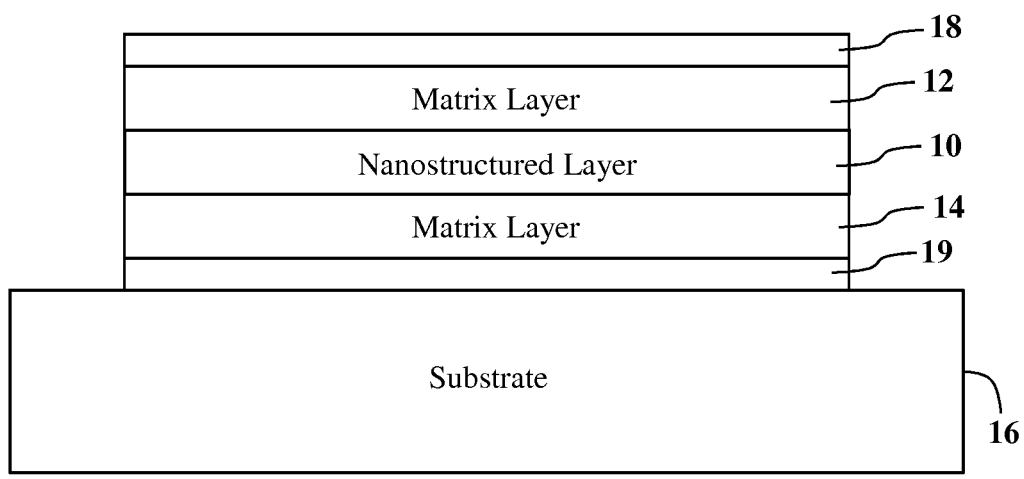
FIG. 1A is a simplified schematic of another multilayer sensor.

FIG. 1 is a highly simplified schematic of a multilayer structure, in which a matrix layer 14 is deposited on substrate 16, a nanostructured layer (in some examples, of a ferromagnetic material) is then deposited on the matrix layer, and a second matrix layer is deposited on the ferromagnetic layer. The number of layers may vary from 2 to 100. In representative examples, the matrix material is a semi-metal layer, and the nanostructured layer is a ferromagnetic metal such as cobalt. First and second electrodes shown schematically at opposed ends of the multilayer structure (18, 19) may be used to monitor electrical resistance, either in a direction parallel to the layer planes as shown in FIG. 1 or perpendicular to layers as shown in FIG. 1A. In the later case, an electrode layer 18 may be located between the first matrix layer (14) and the substrate (16), and a second electrode layer 19 formed on the topmost exposed matrix layer (12 in FIG. 1, though a solid-state structure may include many more nanostructured/matrix alternating layers.)

The nanostructured layer may comprise nanostructures of a metal that self-assembles into discrete nanostructures when deposited on the matrix layer 14, for example due to surface self-assembly of a first material. During aging processes, the nanostructures may partially melt, and form a conducting pathway between the electrodes. If the matrix material conductivity is significantly less than the nanostructured material, for example at least one order of magnitude less at an operating temperature, the formation of physical interconnections such as nanowires between formerly discrete nanostructures causes the conductivity to fall. (Here, conductivity refers to the electrical conductivity).

Figure 2:
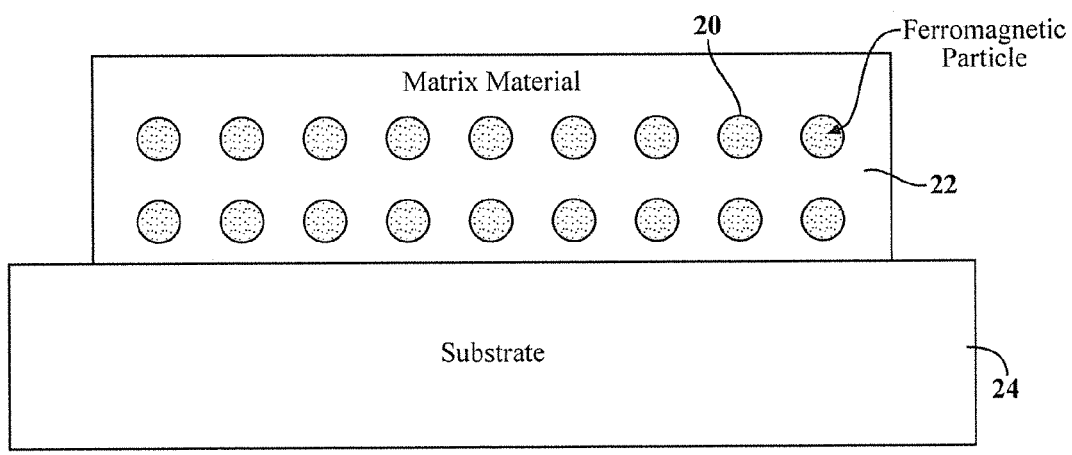
FIG. 2 is a schematic of an array of ferromagnetic particles within a matrix.

FIG. 2 is a simplified schematic whereby ferromagnetic particles 20 are dispersed through a matrix. The structure is supported by a substrate 24. The properties of this configuration will be discussed in more detail later on in the specification.

Experimental examples described below used cobalt as the ferromagnetic metal and antimony (Sb) as a semi-metal matrix. However these are exemplary and other ferromagnetic metals and matrix materials may be used. Any appropriate matrix material may be used, such as silicon or alumina ($Al_2O_3$), or in some examples flexible substrates such as metal foils and polymers.

Experimental examples were fabricated in which Sb was a semi-metal matrix layer, and Co was used as a nanostructured ferromagnetic metal layer. FIG. 1 apparently simplifies the multilayer solid-state structure considerably, as discussed later in relation to STM observations. In discussing layer thicknesses, the nominal layer thickness corresponds to that which would be obtained for a uniform layer thickness. In practice, the ferromagnetic metal tended to aggregate and form nanostructures in the form of nanoscale flakes within the matrix material. The thickness of these nanoflakes may exceed the approximate layer thickness estimated from the amount of deposited material, due to plumping of the material. Nominal layer thicknesses may be in the range 0.5 nanometers to 10 nanometers.

The ferromagnetic metal may form self-assembled nanoparticles within the structure. STM observations revealed that some particles may be 4 nanometers thick, for a nominal 1.5 nanometer layer thickness. This is evidence of surface self-assembly of the cobalt layer on the antimony layer.

Other matrix materials may be used, such as other semi-metals including tin and bismuth, or other semiconductors or insulator. In some examples the matrix layer need not be a semi-metal layer, and may in some cases have a resistance that is much higher than the ferromagnetic metal. This allows greater resistance changes to be obtained.

In experimental fabrication examples, Sb and Co were alternately deposited on a silicon substrate. The Sb layer covered the substrate quite well as discussed in more detail later, and observations of the cobalt layer deposited on Sb showed that the cobalt tended to grow into each other right away by a self-assembly mechanism. The aging process in these experiments appeared to be a morphological change, by which magnetic attractions between the ferromagnetic cobalt particles induced melting together of nanoflakes and formation of nanowires. Electrical conductivity is better through cobalt nanowires than through the matrix material, so that resistivity decreases.

In some examples, the ferromagnetic metal nanoparticles flow together, and may push away intervening matrix material.

Figure 3:
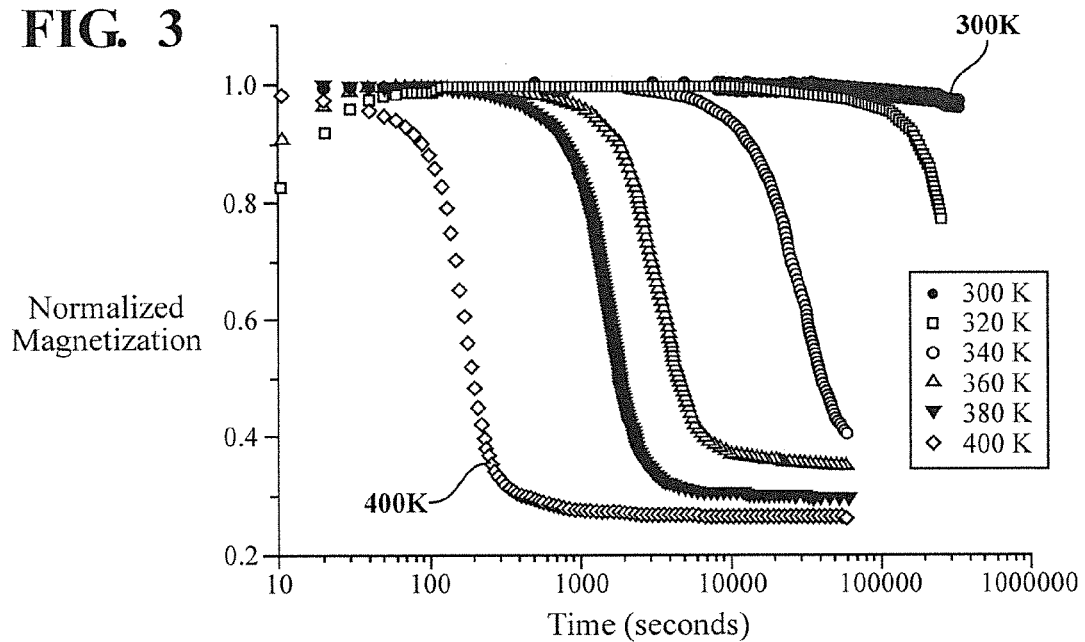
FIG. 3 shows normalized magnetization as a function of time and temperature for an antimony/cobalt (Sb/Co) multilayer structure.

FIG. 3 shows variation in the normalized magnetization as a function of time. The figure shows normalized magnetization decay curves for temperatures ranging from 320 K to 400 K, for samples deposited at 335K on the 111 face of Si and with curves normalized to their maximum value. The figure shows that the magnetization decay is large, and may account for 70% of the magnetization. The inflection point of the decaying portion may be used to define a characteristic time, $\tau_i$.

The characteristic time is highly sensitive to the deposition temperature of the magnetic multilayer. Hence, aging sensors can be fabricated for a wide variety of applications, and the characteristic time may be selected according to the aging process of the monitored physical system.

The nominal layer thickness of the monitored multilayer was Co/Sb 1.5 nanometers/2.5 nanometers. Aging decays in samples with 10 layers, 50 layers, and 100 layers were analyzed and showed similar effects. The characteristic time was estimated to be approximately 3 weeks for samples deposited at 35° C., and approximately 6 months for samples deposited at 50° C., for storage at room temperature. When not in use, samples were stored at liquid nitrogen temperature to avoid aging occurring.

FIGS. 4A-4D show the effect of deposition and annealing time on the resistance changes in a magnetic multilayer. The figures show normalized resistance decay curves ($R/R_{max}$) measured in a magnetic field of 0.01 T for temperatures from 320 K to 400 K, for samples deposited at 335K on the 111 face of Si with curves normalized to their maximum value. R represents the resistance at a certain degree of aging (a function of time and temperature, as shown), and $R_{max}$ is the resistance of an initial state before significant aging processes. An electronic circuit can be used to provide an alert (e.g. visual and/or audible) when the normalized resistance falls to a predetermined value).

Figure 4A:
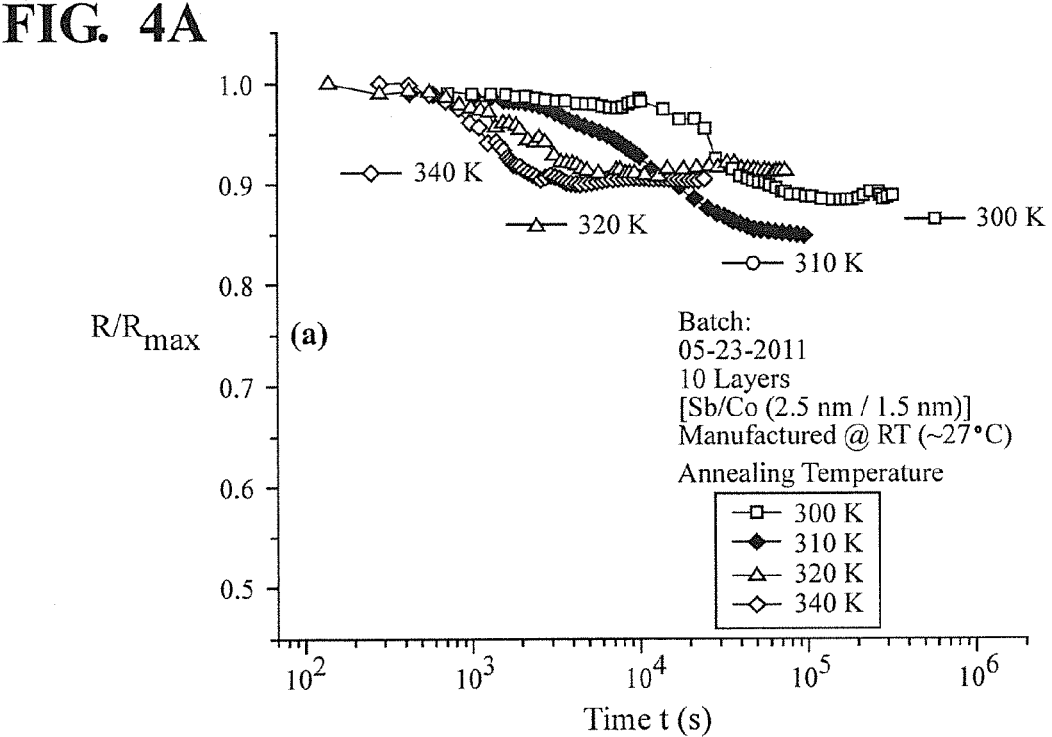
FIGS. 4A-4D show electrical resistance changes as a function of deposition temperature and annealing temperatures, for a Sb/Co multilayer structure.

FIG. 4A shows samples manufactured at near room temperatures (27° C.) and subsequently annealed at 300, 310, 320, and 340 Kelvin (K). For room temperature deposition, little resistance change was observed.

Figure 4B:
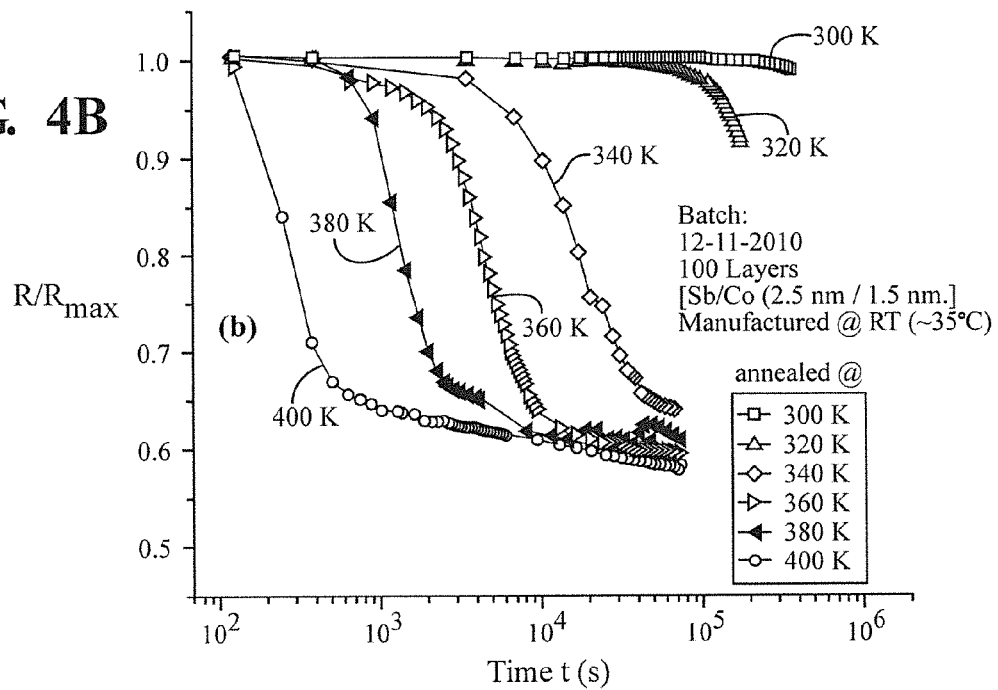

FIG. 4B shows results obtained for a sample manufactured at 35° C. This figure shows that these samples can show appreciable electrical resistivity changes, in some cases over 40%, and the figure further shows that the characteristic time may be adjusted by an annealing step to the desired time. For comparison, FIGS. 3 and 4B display aging decay curves for the magnetization and normalized resistance (respectively) as a function of temperature for samples deposited at 35° C. An external magnetic field of 0.01 T was applied during both of these measurements.

Figure 4C:
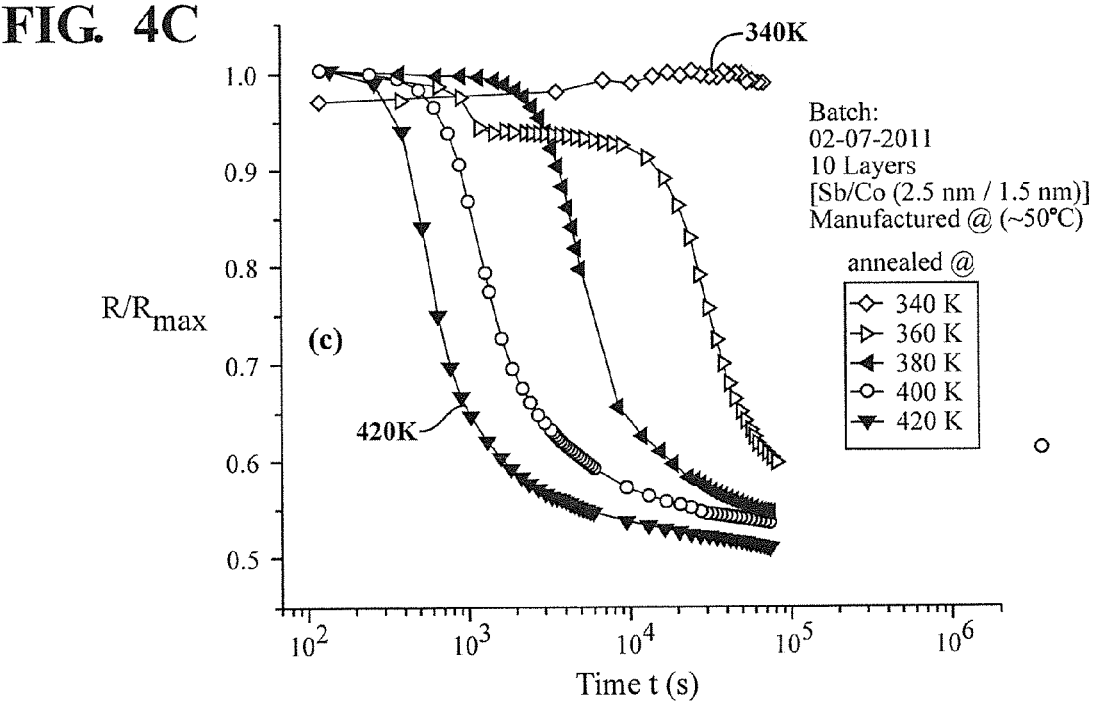

FIG. 4C shows electrical resistivity changes for a magnetic multilayer manufactured at 50° C. Again, a subsequent annealing step has considerable effect on the resultant behavior. The higher the annealing temperature, the shorter the characteristic time. The annealing step used temperatures of 340 Kelvin-420 Kelvin at 20K intervals.

Figure 4D:
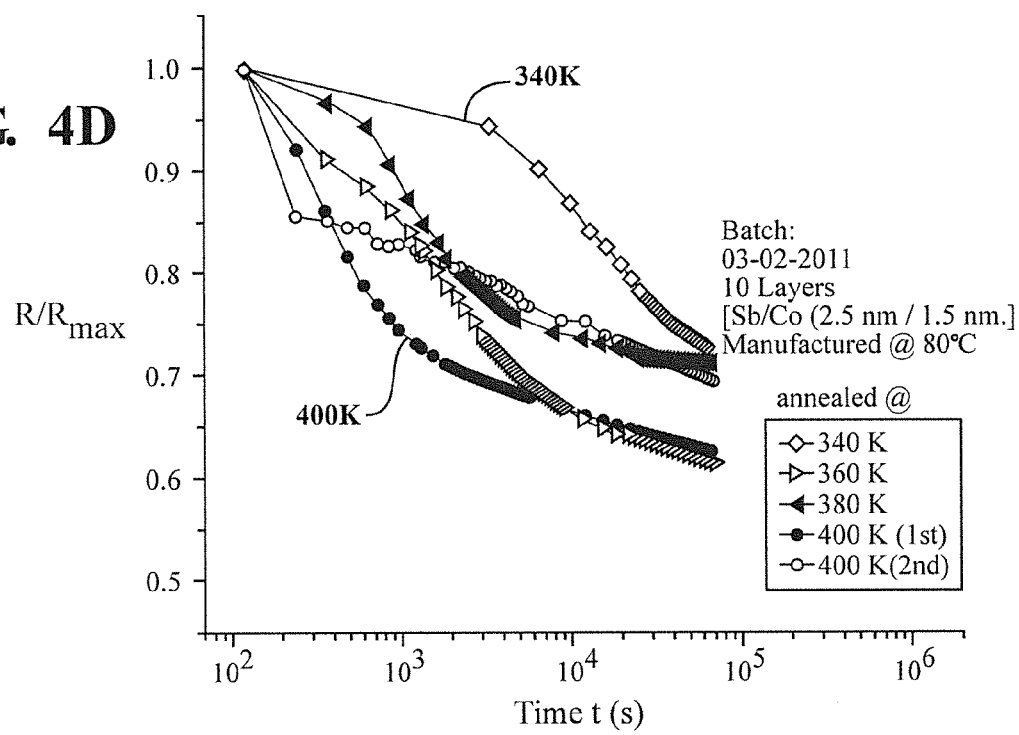

FIG. 4D shows a sample fabricated at 80° C., with annealing at different temperatures. In this case performance was relatively poor, compared to FIG. 4C, but still may be usable.

In aging experiments, the aging decays may be characterized by two timescales. The first time scale represents birth or the beginning of aging while the second time scale represents how fast the system ages. For these experiments, we set the birth timescale (t=0 s) to the time when the sample was placed in the preheated cryostat, the field turned on and the measuring program initiated. The inflection point of the decay curves, as observed on the logarithmic scale, provides a second timescale that quantifies the rate of aging. For both the magnetization and resistance this time is denoted $\tau_i$. At this time the function $S(t)=dA(t)/d\ln(t)$ (where A(t) is the decaying signal) produces a maximum. Both the magnetization and resistance (at 0.01 T) of the Co/Sb system undergoes an aging decay which shifts significantly as a function of temperature. For a sample deposited at 35° C. the magnetization curves undergo a total decay of approximately 60-80% of the initial magnetization. Every increase of 20K brings a ≈5-10 fold increase in $\tau_i$. The resistance displays a decay of approximately 40% of the initial resistance.

FIGS. 5A-5F show a hysteresis study of a Co/Sb multilayer. A sample was deposited at 350K on the 111 face of Si and aging performed at 400K monitored, where hysteresis curves labeled A-B-C-D correspond to time points along the aging curve of FIG. 5D.

These figures show an experimental analysis of hysteresis loops taken at various times during the aging decay process. Experimental analysis of the hysteresis loops of states taken at various times through from the pre-aged and post-aged states shed insight on possible mechanisms for the magnetization decays.

Results were obtained for a single Co/Sb sample fabricated at 50° C. on the 111 face of silicon. Aging was performed at 400 K. In this description, unless otherwise indicated, deposition temperatures are given in Celcius and aging temperatures given in degrees Kelvin. The as-assembled magnetization decay of FIG. 5D was measured in a magnetic field of 0.01 Tesla and the indicated points A, B, C and D indicate the points where the corresponding hysteresis points were taken at 300 K. For example, the curve of FIG. 5A was obtained at point A shown in FIG. 5D. The hysteresis loops of unaged samples have a ferromagnetic signature with a coercive field of approximately 0.006 Tesla. The unaged sample (FIG. 5A) also has a remanent magnetization of approximately 1.1 memu.

While the coercive field remains similar in the aged samples, the remanent magnetization decreases to 0.8 memu and the slope in the high field magnetization increases. These changes may be indicative of a possible paramagnetic or frustrated contribution. After aging well past the rapid decay phase and into the slower and possibly logarithmic decay, the in-plane hysteresis again shows ferromagnetism with a reduced saturation moment. The out-of-plane magnetization, which displayed a ferromagnetic behavior before aging, has a somewhat noisy paramagnetic signature after aging. It is possible that there is significant demagnetization in the out-of-plane data.

The results showed a total magnetization decay of approximately 50% of the maximum magnetization while the total resistance decay was close to 40% of the maximum. The sample was aged at 400 K for set periods of time and the magnetization decay measured. After aging, the sample was removed from the cryostat to room temperature. The cryostat was then cooled to 300 K and the sample placed back in the cryostat for the hysteresis measurements at 300K.

Figure 5A:
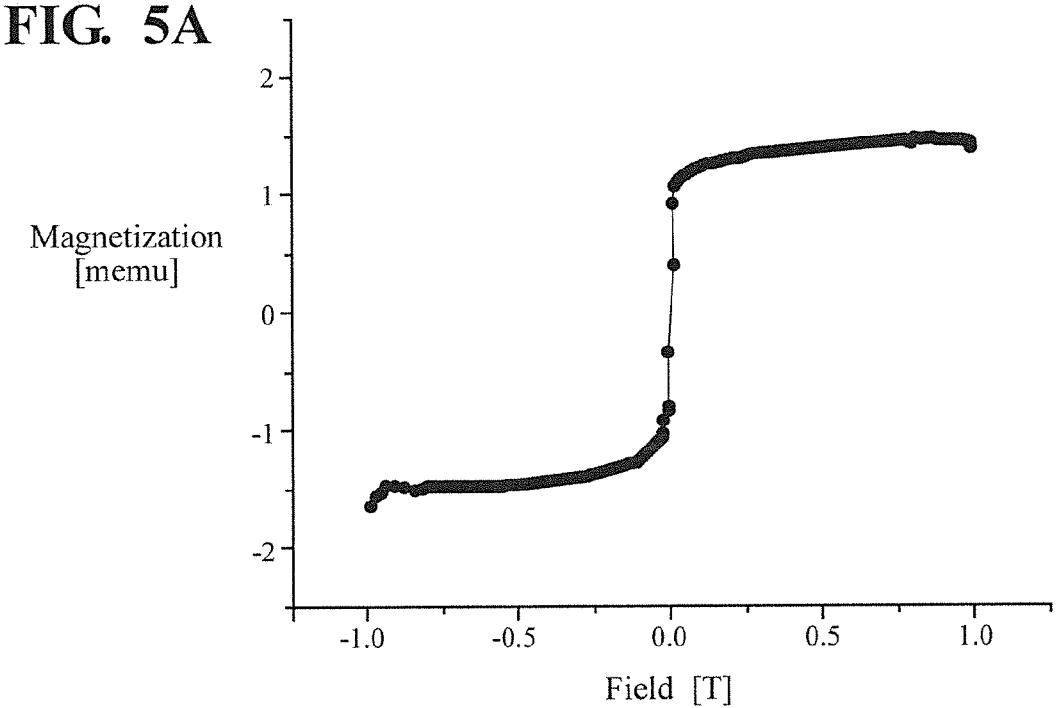
FIGS. 5A-5F show a magnetic hysteresis study of a single magnetic multilayer.
Figure 5B:
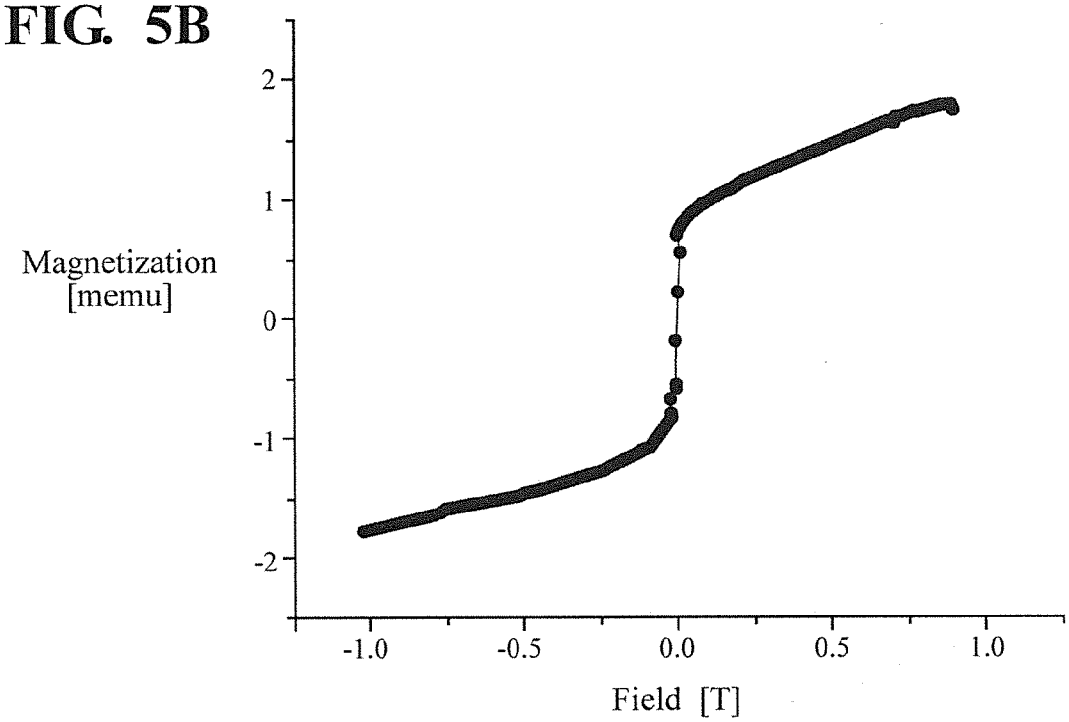

During hysteresis measurements the sample would often be held at 300K for up to 12 hours. At 300K the estimated characteristic time is on the order of six months aging would be slow enough to ignore the effects due to aging during the hysteresis measurements. This retardation in time scale is evident in FIG. 5D, where the segments making up the set of decays measured at 400K are reconstructed into a single decay. The hysteresis loops of the pre-aged samples have a ferromagnetic signature with the coercive field of approximately 0.006 T. The unaged sample also has a remanent magnetization of 1.1 emu and a slight increasing slope in the high field regime. At 1 T the magnetization reaches a maximum of approximately 1.4 emu. After aging at 400K for 600 s, changes in the hysteresis loops were immediately observed (FIG. 5B). While the coercive field remains similar to the unaged sample there is a distinct tilt to the hysteresis loop, the remanent magnetization decreases to 0.8 emu and the slope in the high field magnetization increases. These changes are indicative of a possible paramagnetic or frustrated contribution. Both of these effects are accentuated with further aging.

Figure 5C:
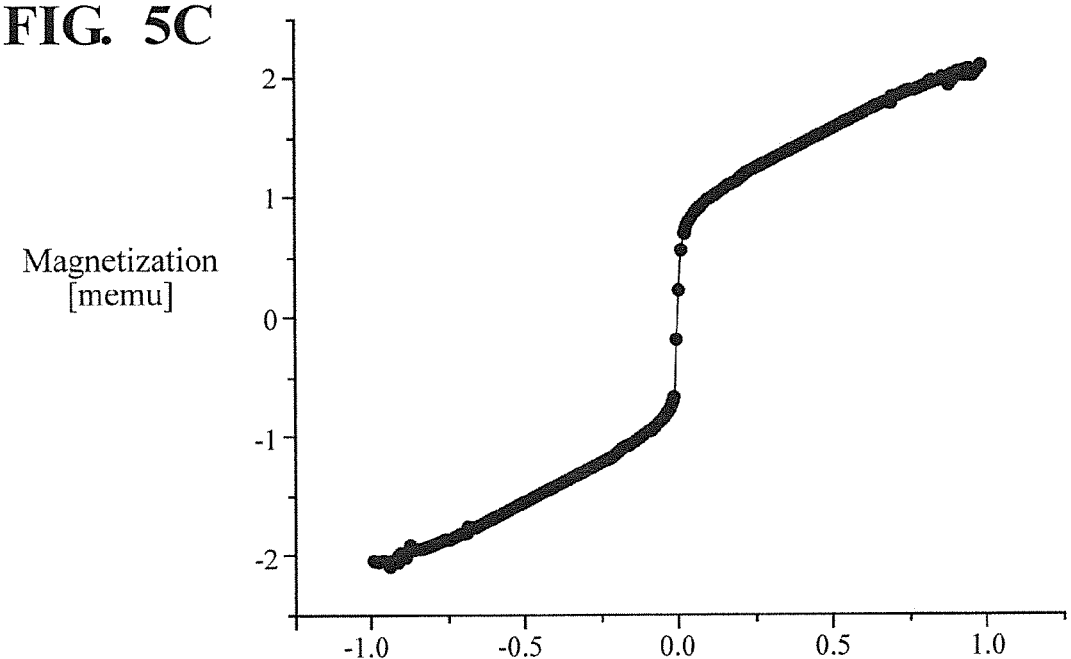
Figure 5D:
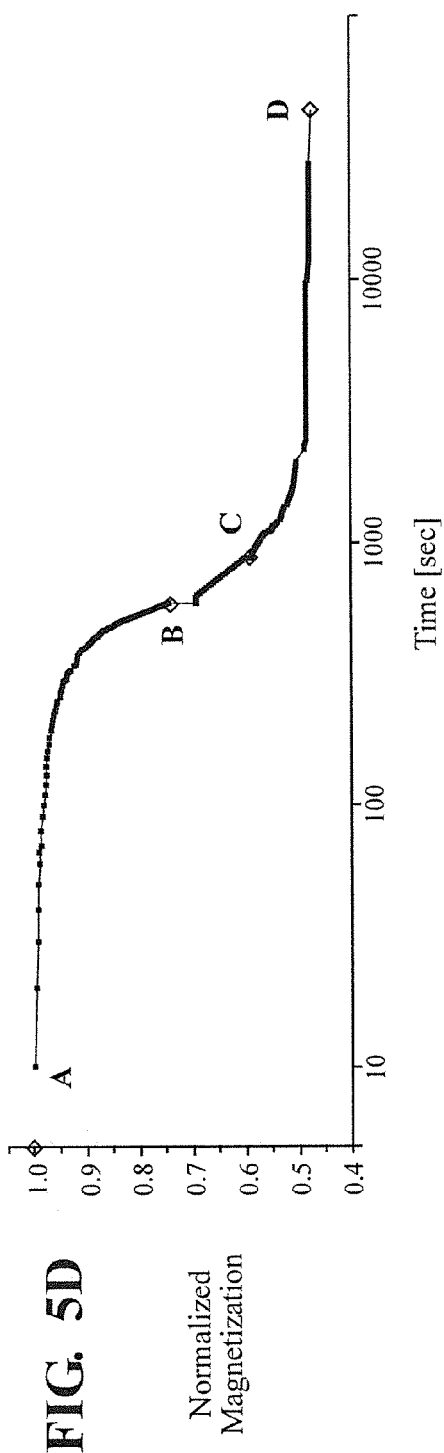
Figure 5F:
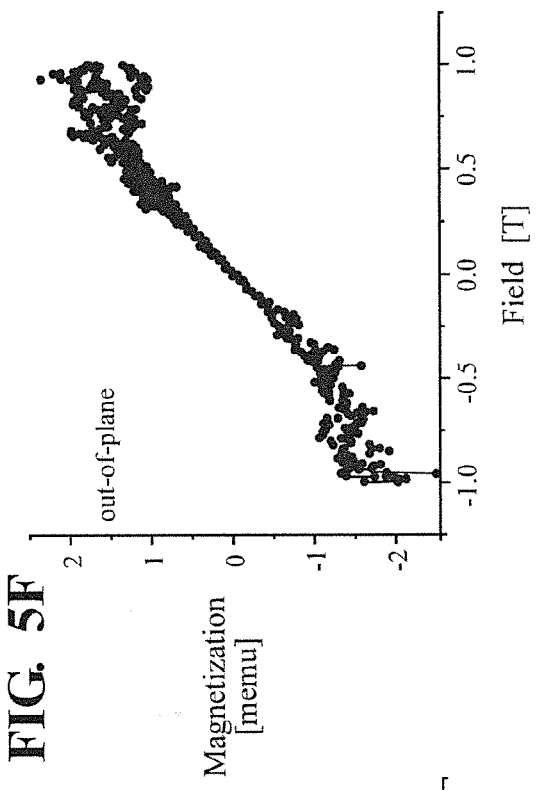
Figure 5E:
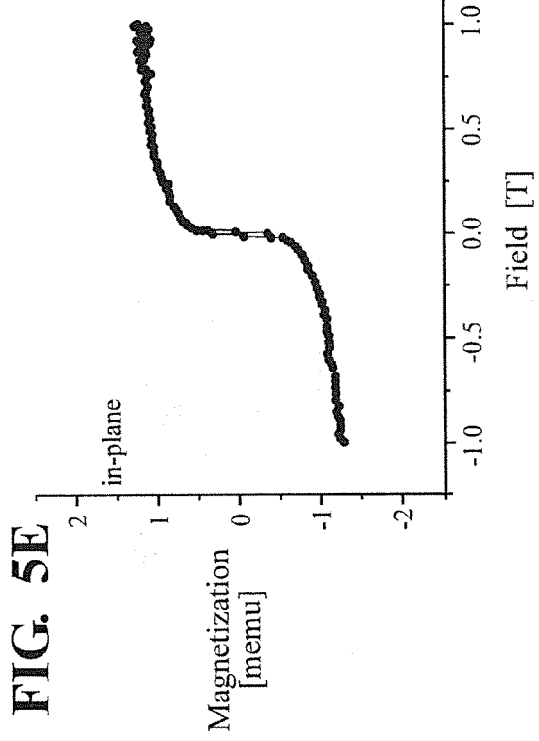

FIGS. 5B and 5C are taken during the rapid decrease in the magnetization. This data also lends credence to the argument that the decrease in the magnetization is not due to loss of moment through chemical bonding to O, Si or even the Sb. Chemical bonding would reduce the saturation moment and we would expect that the net moment (nominal saturation magnetization) in high field would decrease. After aging well past the rapid decay and well into a much slower, possibly logarithmic decay, the in-plan hysteresis again shows ferromagnetism with a reduced saturation moment. The out-of-plane magnetization, which showed a ferromagnetic behavior before aging interestingly, in this sample, has a paramagnetic signature after aging.

One explanation is that before aging the nanoflakes behave as single domain ferromagnetic particles. As the samples age, these flakes begin to melt, flow, and contact each other. As nanowires form, the enhanced size increases the demagnetizing field, possibly inducing anti-parallel alignment of domains and the formation of domain walls. This is a probable mechanism for reducing magnetization during aging.

In the initial stages of nanoflake contact, the energy of a domain wall is minimized if it forms at the smaller contact interface as opposed to in the interior of the particle. Also, the c axis of nanoflakes is likely misaligned in the initial contact, possibly leading to frustration between moments. This may cause the tilting of the hysteresis loops during the aging process.

Figure 6:
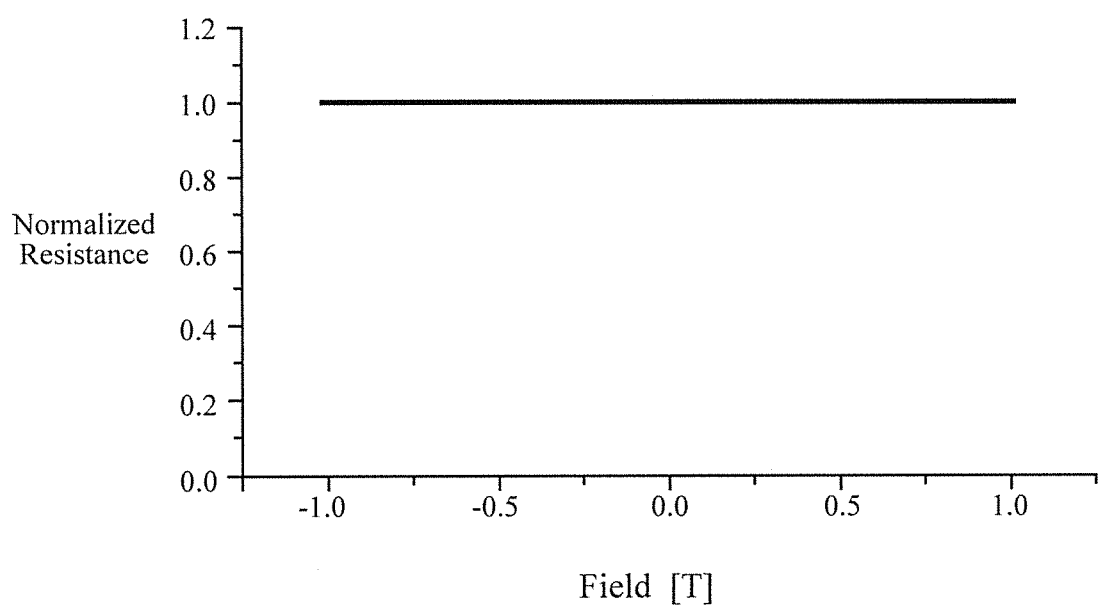
FIG. 6 shows magnetic field independent magnetoresistance for a Co/Sb multilayer, indicating that a resistive effect is observed, rather than a magnetoresistive effect.

FIG. 6 shows the normalized resistance as a function of external magnetic field. This figure shows that the resistive effects observed in this magnetic multilayer are not magnetoresistance effects. Even though a magnetic/metallic multilayer may appear to be a GMR system, it is not reacting to an external field as one. Even though the majority of the resistance decay measurements reported here were made in 0.01 T, to remain consistent with the magnetization measurements, similar decays were observed in zero magnetic field. Therefore the response is a resistive effect, not a magnetoresistive effect.

Figure 7A:
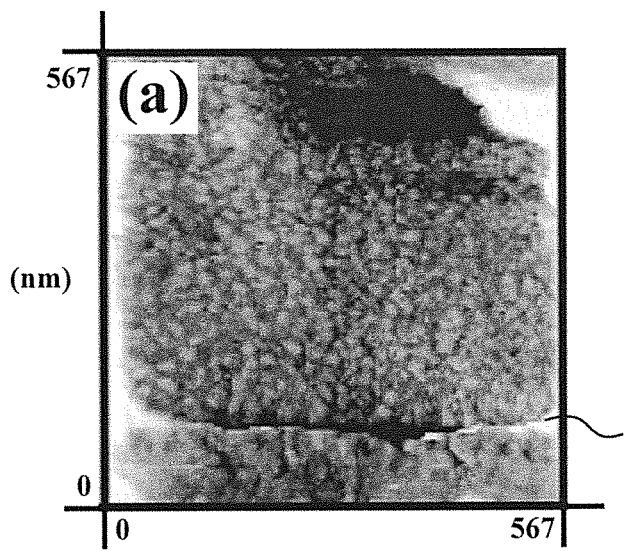
FIGS. 7A-7C are further images of the effect of aging on the magnetic multilayer.
Figure 7B:
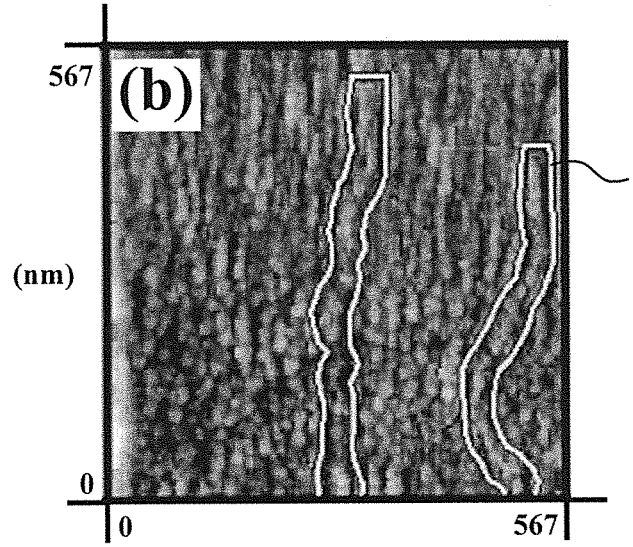
Figure 7C:
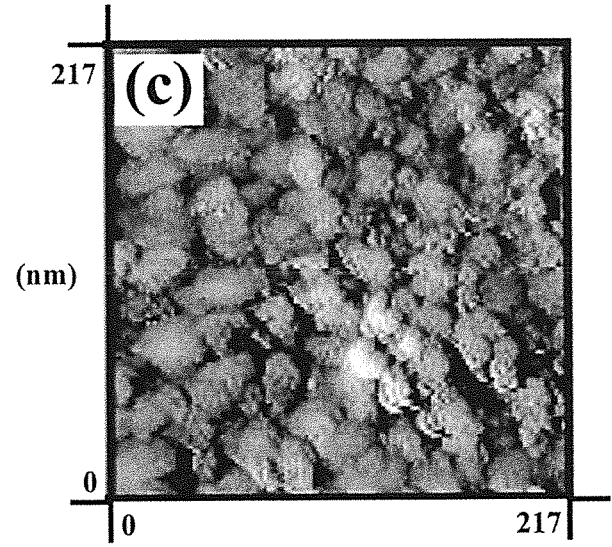

FIGS. 7A-7C show STM images. FIG. 7A is an STM image of a pre-aged Sb/Co/Sb magnetic multilayer. The Sb layers were nominally 2.5 nanometers thick, and the Co layer was 1.5 nanometers thick. As the Sb layer thickness increases, electrical resistance of the solid-state structure increases. As the Co layer thickness increases, the time scale may increase. In this context, pre-aged means before aging processes are significant.

FIG. 7A shows the Sb layer on a silicon substrate, and shows a microcrack 100 near the bottom of the sample. However, this was atypical and microcracks were not generally observed so that dislocations are unlikely to be a source of the electrical resistivity changes. The images show the microcrack 100 near the bottom of the image, and a film edge on the right-hand side. The Sb layer wets the surface of the substrate and provides a generally uniform coverage. The Co particles appear to be observable through the upper Sb layer.

FIG. 7B shows an STM image of the same sample after aging, after which the cobalt layer has changed morphology. A comparison of FIGS. 7A and 7B, which are from the same sample, shows that the results of aging are directly observable. FIG. 7B is the same sample but a different area as that shown in FIG. 7A, after being heated to 400K for 20 minutes. This is approximately the same time as required for fully aging, i.e. full decay of the fast decaying portion of the magnetization and resistance curves. There are dramatic morphological differences. The Co layer has crept anisotropically through the Sb layer, forming long nanowires 102. These nanowires provide an improved conductivity path through the nanostructured layer.

Examples of the present invention also include improved methods of forming nanowires, for example through the melting and physical interconnection of nanostructures in a nanostructure/matrix multilayer solid-state structure, and improved nanowires formed by this process. Semiconductor devices using quantum size effects for modified electrical or optical properties may be fabricated using this approach.

Statistical analysis of the nanowires determined a mean width of 15 nanometers and lengths from 100 nanometers up to 570 nanometers. The maximum length measurements were limited to image size. The nanowires had a mean length of 330 nanometers with a standard deviation of 130 nanometers, the nanowire thickness being approximately 2.3 nanometers. Apparently, there was significant overlap between the nanowires along both their lengths and widths, and they may be in electrical contact. The directionality of the wires is observable but not presently understood.

Analysis of the Co particles suggested a Gaussian distribution of sizes, with a mean maximum length of 19 nanometers and a standard deviation of 5 nanometers. The nearest neighbor distribution was estimated as a mean distance of 4.0 nanometers with a standard deviation of 1.7 nanometers. Profile analysis indicates that the Co particles were on average 2.5 nanometers in height. The lateral dimensions are much larger than the thickness, and the particles are effectively nanoflakes. The Co attains approximately 50-70% coverage. The nanoflakes were self-assembling and had a large surface-to-volume ratio.

FIG. 7C shows an Sb/Co single bilayer system, where Co is the top layer deposited at 50° C. The sample was removed from the deposition chamber and stored for a period at 77 Kelvin, to prevent aging, and then studied at room temperature after warming up for 2 hours. The image shows nanoparticles approximately 30 nanometers in size and 1.6 nanometers in thickness, producing 91% coverage and apparently overlapping. The aging process appears isotropic, and in this case, apparently, the Sb layer confined the nanoparticles, slowing down migration and producing the time-dependent effects.

Figure 8A:
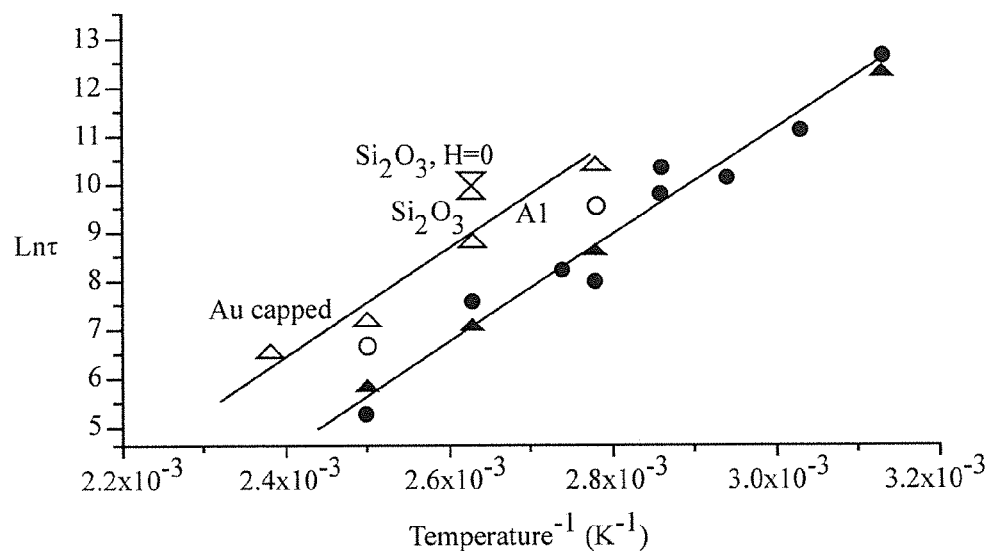
FIGS. 8A and 8B illustrate activated dynamics analysis of the aging process.
Figure 8B:
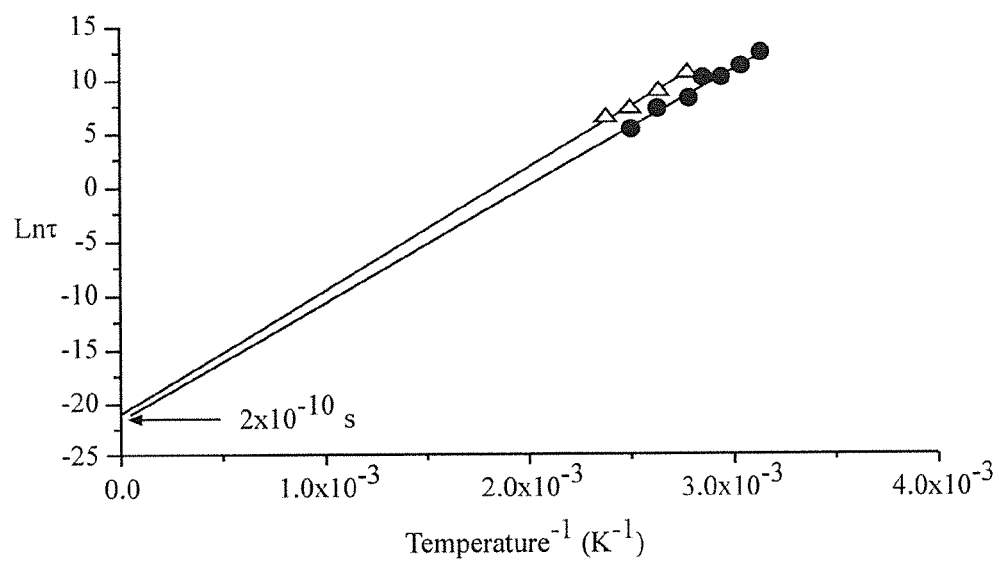

FIGS. 8A and 8B show an activated dynamics analysis of the aging process. FIG. 8A shows the natural log of the characteristic time against reciprocal temperature. The data is shown for two samples deposited at 35° C. and 50° C., the characteristic time being determined from the inflection point of the decay curves. FIG. 8A shows ln $\tau_i$ vs. 1/T for all samples measured, where (unless indicated) all samples were deposited on the 111 face of Si and measured in a field of 0.01 T. The lower line indicates samples deposited at 35° C., and the upper line indicates samples deposited at 50° C. Circles are $\tau_i$ determined from magnetization data, triangles are $\tau_i$ values determined from resistance data.

FIG. 8B shows ln $\tau_i$ vs. 1/T for all samples measured in this report. Unless indicated, all samples were deposited on the 111 face of Si and measured in a field of 0.01 T. The lower line indicates samples deposited at 35° C., and the upper line indicates samples deposited at 50° C. Circles are $\tau_i$ determined from magnetization data, triangles are $\tau_i$ values determined from resistance data. Characteristic times were obtained from both magnetization and resistance decays. This figure shows how characteristic time is controllable by adjusting the deposition parameters. For the sample deposited at 35° C. the activation energy was determined to be 0.91 eV.

FIGS. 9A-9B show example electronic circuits including a battery 206, switch 200, sensor 202, and light emitting diode (LED) 204. An LED may have an associated current-limiting series resistor (not shown for clarity). In FIG. 9A, the LED illuminates when the switch is closed, as long as the resistance of the sensor 202 has not fallen enough so that it provides an alternative current path. FIG. 9B shows a series configuration, where a fall in resistance due to aging may cause the LED to light. These circuits can be configured so that the light turns on or off as an aging threshold is reached. The effect may use an internal battery as shown, other dedicated power supply, or in some cases may use an external source of power. In some examples, an electronic circuit includes a GMR sensor, which is responsive to magnetization changes in a proximate aging sensor. The resistance changes of a GMR sensor may be detected in an analogous manner to the electrical resistance changes of an aging sensor.

FIG. 9C shows a simplified schematic allowing modification of resonant circuit 220 using sensor 222, whereby capacitive or inductively-coupled transponders may be used to provide a characteristic frequency which changes as the resistance of the sensor changes. In some cases, wireless interrogation of the transponder may be used, for example by using the sensor to switch a reactive or resistive component out of the resonant circuit. In other examples, conventional analog circuits (such as operational amplifier circuits) can be used to determine when a threshold degree of aging has occurred.

An example sensor includes a sensor material and electrodes configured to make electrical contact with the sensor material, such as a solid-state structure as described herein. For example, a sensor material may be formed as a strip, with electrical contacts at each end of the strip. The strip of sensor material may be formed on a substrate, which may be adhered to a surface close to the item to be monitored. The sensor material may be enclosed in a housing, having terminals in electrical contact with the electrical contacts. In a multilayer structure, the electrical resistance changes may be detected in a direction parallel to the layer planes (as in the experimental examples discussed above.) In other examples, electrodes may be configured to detect electrical resistance changes perpendicular to the layer planes. The solid-state structure may be supported by a substrate. Aging-correlated electrical resistance changes were observed using silicon (Si), alumina (Al2O3), and plastic (Mylar) substrates. Hence, in some examples, the substrate may be a rigid planar substrate such as a dielectric substrate. In some examples, the substrate may be a flexible polymer substrate. An adhesive layer (for example, on the opposite side of the substrate from the solid-state structure) may be provided to adhere the sensor to an item for aging monitoring of the item.

Discussion of Experimental Data

The time and temperature dependence of the decays in these samples indicate that the process may be thermally activated. In nature when a system in one state can transition to another state by a thermally activated hoping over an energy barrier to another state the system can generally be described by an Arrhenius law. The Arrhenius law, as written for chemical dynamics, determines a frequency of transition between states at temperature T. This law was generalized by Neel to the Neel-Arrhenius form to describe the characteristic spin flip time (barrier hopping time) of superparamagnetic nanoparticles:

$$\tau = \tau_o \exp(E_a/kbT) \qquad (1)$$

In this equation, $E_a$ is the activation energy or barrier height, $\tau_o$ is the fluctuation timescale and $\tau$ is the characteristic hopping time at temperature T. In the case of superparamagnetic particles, $E_a=KV$ where K is the anisotropy constant and V the particle volume.

A second and more likely scenario, considering the change in morphology, is thermally activated melting of the nanoflakes. Nanoparticle melting is a known effect and can be a nuisance when it comes to producing electronic contacts. The large surface to volume ratio of these flakes should strongly enhance melting. The nucleation and growth of crystallites during annealing is discussed in Rios et al., Mat. Res., 8(3) (2005).

The STM images suggest that one and likely two growth mechanisms are present. The nanoflakes are apparently migrating through the intervening Sb to couple to each other. The model for the velocity of the interface of high angle boundaries is thermally activated. Driving and retarding forces to this mechanism have also been considered. Second, once the Co crystals form an interface, the process of coalescing can reduce the free energy by including a rotation of the crystal axis of one of the particles to form a single crystal. While both of these mechanisms have been applied to annealing of polycrystalline samples it is likely that they can also be applied to the Co/Sb system.

Plotting ln $\tau_i$ vs. 1/T for two sets of samples deposited at 35° C. and 500° C. Samples deposited at 35° C. include sets of $\tau_i$ values from both magnetization and magnetoresistance decays. It can be observed that both sets of data are compatible. Fluctuations in $\tau_i$ data provide a better metric of the reproducibility of time scales then say the error in the determination of $\tau_i$, which are generally small. It would appear that, within the constraints of the percolation limit and smaller nanoparticle fluctuation time scales, that a range of characteristic time scales may be achieved, at a single temperature, by depositing the samples at different temperatures. FIG. 3B is the same plot 1 as FIG. 3A but with the fit extrapolated to T→0. This extrapolation gives the value of $\tau_o$, the thermal fluctuation timescale. The value of $\tau_o$ obtained for fits over samples from the two deposition temperatures is approximately $1\text{-}4\times10^{-10}$. This is consistent with timescales obtained from magnetic susceptibility data for single domain Ni. From the graph of sample deposited at 35° C., an activation energy of 0.91 eV is found.

The measured resistivity of the pre-aged sample is approximately one order of magnitude greater than what we would expect from a calculation of the expected resistance of this particular multilayer sandwich. FIG. 7A shows a microcrack near the bottom of the sample. A sample with large numbers of dislocations or a fractured sample could produce a large resistivity but as previously mentioned, the number of cracks observed was minimal, and surface profiling suggests that the Sb forms a contiguous layer, so it is unlikely that dislocations are the reason for this enhanced resistance.

Two effects may contribute to raise the resistance of the Co nanoflakes to the flow of conduction electrons. In a normal metal, current is carried equally by both electrons of both spin components. In a ferromagnetic, current is carried preferentially by the majority spin component. At a ferromagnetic/non-ferromagnetic metal interface, this mismatch produces an electrochemical mismatch that increases the boundary resistance. Spin orbit scattering off of the interface is also likely to contribute to the resistivity. Upon the advent of aging, the nanoparticles begin to flow into each other. An electron needs to only cross one interface to enter the extended low resistivity cobalt nanowires where it can be transported with little resistance for hundreds of nanometers. This is likely the short-circuit which decreases the resistance.

There are many mechanisms that can cause a decrease in the magnetization. The hysteresis measurements as well as the STM data provide clues as to the magnetization decrease during aging. First, the preaged samples look ferromagnetic. While super ferromagnetism is a possibility magnetization vs. temperature studies down to 10K, show no evidence of the ultra small paramagnetic particles forming between the nanoparticles during the deposition as observed in $CoFe/Al_2O_3$. As a matter of fact the saturation magnetization can be fit to the standard $T^{3/2}$ form between 10K and 300K. The STM results indicate nanoparticles that are extended in-plane (~15-25 nm) while the out of plane thickness is only ~3-4 nm. The in-plane magnetization is more than three time greater than the out of plane magnetization. This geometry significantly decreases the demagnetizing field, stabilizing the particle against domain wall formation. Therefore, it is likely that the nanoflakes behave as single domain ferromagnetic particles. As the samples age these flakes begin to come in contact with each other. As the nanowires begin to form it is likely that the enhanced sizes will increase the demagnetizing field and the domain walls will form.

In the initial stages of nanoflake contact two factors must be considered. First, in the in initial contact the energy of a domain wall would be minimized if it formed at the much smaller contact interface as opposed to in the interior of a particle. Second, the c-axis of the individual nano flakes are likely misaligned in the initial contact which may lead to frustration between the moments. It is likely that this frustration is the cause of the tilting of the hysteresis loops during aging. The out-of-plane paramagnetic signature observed in the heavily aged sample is interesting and suggests that $Sb_3Co$ may be forming at the nanowires interface.

Sample fluctuations may also influence the accuracy of time dependent data. A time dependent decay may be used in various applications as a clock and a switch. However, the experimental fluctuations in $\tau_i$ reduces accuracy of timing applications. The e-beam evaporator used effectively produces a point source of evaporating atoms and the substrates were laid out in a plane bisecting the sphere of that source. Sample to sample deviations are therefore to be somewhat expected. Variations in nanoflake sizes and separation distances also likely contribute to inhomogeneities in the time scale. There are a variety of techniques available for controlling sample sizes (Majetich et al., "Magnetostatic Interactions in Magnetic Nanoparticle Assemblies: Energy, Time, and Length Scales," J. Phys. D, 39, R407-R422, 2006), and separations (Jun et al., Accounts of Chemical Research, 41(2), 179189, 2008) in spherical nanoparticles which may be modified for use with examples of the present invention.

Further Discussion of Sample Preparation and Handling

The samples used in the study were deposited in a vacuum of $\leq 1\times10^{-6}$ Torr in an Edwards model 2033 e-beam evaporator. The deposition rate was monitored in situ during the entire course of the deposition with a deposition monitor. Deposition rates were approximately 0.2-0.3 nm/minute. The majority of the samples discussed herein were produced through deposition on the <111> face of silicon, although data is reported for a few samples deposited on $Al_2O_3$, as well as deposited on common commercial aluminum foil. As the Edwards evaporator has a single e-beam gun, multilayer samples were produced by evaporating the Sb and then rotating the Sb 99.999% target out of the gun and the Co 99.9% into the gun to produce a layer of cobalt. Co nanoparticles were produced in the solid-state within a metallic environment. Co is known to form magnetic nanoparticles in a variety of environments and has a bulk resistivity of 62.7 nΩ·m at 300 K.

Bulk Co has a melting temperature of 1,495° C. Sb is a semimetal and has a bulk resistivity (417 nΩ·m) almost seven times higher that of Co. Bulk Sb has a melting temperature of 630.74° C. We waited approximately 5 minutes after the Co was deposited in order to maximize time for possible Volmer-Weber particle growth mechanisms to act. Samples were made with nominal layering of Co/Sb 1.5 nm/2.5 nm. Samples with 10 layers, 50 layers and 100 layers were made, and all showed reasonably similar effects. Unless specifically mentioned, all data represent measurements on separate samples.

Special care was used for the handling and storage of materials that show aging properties at room temperature. Samples with 10 layers took about two hours to make. As the number of multilayers increased to 50-100 layers, depositions could extend over several days. Aging presumably begins during the deposition process, but for these samples the aging at room temperature was quite slow, with a characteristic time estimated to be approximately 3 weeks for samples deposited at 35° C. Care was however taken to minimize any type of aging that may occur before the sample was actually measured. Once removed from the evaporation chamber the samples were placed in an argon glovebox where they were removed from the evaporation sample holder and separately placed in specimen holders in an argon environment. The samples were then stored at 77K. When needed a particular sample was removed, warmed to room temperature in a dry box and either placed directly into the apparatus for magnetoresistance measurements or attached to the sample holder with GE varnish for magnetization measurements. The varnish was allowed to dry for four hours before placing the sample in the LakeShore Model 7307 Vibrating Sample Magnetometer (VSM) with Magnetoresistance (MR) option.

The sample insertion and recording techniques for the magnetization and resistance measurements were slightly different. For the magnetization measurements, the cryostat was preheated to the measuring temperature and the magnetic field was set to 0 T. The sample and sample rod were placed in the cryostat, attached to the head drive, the head drive turned on and an initial zero field magnetization measurement was made. Here, there are some sample to sample deviations. For example, individual zero field magnetization measurements varied from −132 μemu to 300 μemu although most samples had zero-field magnetizations of a few μemu to a few tens of μemu. The largest measured values correspond to values of approximately 10-15% of the maximum magnetization (≈2.2-2.5 memu) obtained once the field is turned on. A 0.01 T magnetic field is then turned on and this sets time t=0 for the aging decay. Once the field is set there is a large rapid rise in the magnetization which maximizes in usually a few tens of seconds. The signal then begins to decay. During the magnetization decay the magnetization was measured every 10 seconds. The measurements reported here were made with both the magnetic field and sensing coils directed into the plane of the multilayers. The out-of-plane magnetic measurements show similar results but with a maximum magnetization of about 25% of the in-plane magnetization. The magnetic moments therefore appear to be directed mainly in-plane. Bulk Co is hexagonal and the easy direction is the c axis, as noted in A. H. Morrish, The Physical Principles of Magnetism, Wiley, New York 1965.

For the majority of resistance measurements the sample and MR probe were inserted into a cryostat, preheated to the measuring temperature and into a preset magnetic field of 0.01 T. Several resistance vs. time measurements were also made in zero magnetic field. Once the program was initiated it took approximately 130 s for the apparatus to take the first point. The measurements reported here are made with the Lakeshore MR Option which is a 4-probe method using 4 in-line tantalum leads to pierce through the multilayers. This geometry leads to the current flowing in-plane and we directed the magnetic field along the current direction. Two measurements (current parallel to, and 180° to the magnetic field) were made and averaged for each point.

After observing the aging decays we attempted to reinitialize the samples to determine if we were dealing with chemical or physical aging. Holding the sample (350° C. deposited) at 400K in 1 T for 24 hours did not reset the sample back to its initial condition. We also tried placing the samples (for short periods of time 10 s-60 s) into a preheated oven over a range of temperatures varying from 700K to 1100K. We were not able to reset the sample and began to conclude that chemical aging was likely.

We set out to eliminate the possibility that chemical aging occurs due to the substrate or due to oxygen annealing. Although solid-state dynamics are arguably too slow (in this temperature range) for Si in the substrate or oxygen (samples were open to air) to diffuse through the 10-250 multilayers in the samples we have made, it was considered. We should also add that either of these scenarios would likely increase the resistance not decrease it. Samples were produced on Si, $Al_2O_3$ and Al foil with similar and consistent decay effects observed. This appears to rule out the substrate as a major mechanism for the decay.

Oxygen could also modify the magnetic moments if it diffused into these thin film samples. Oxygen could enable antiferromagnetic coupling of the Co moments through the superexchange interaction. While we have not been able to rule this scenario out with magnetic experiments, a 100 nm Au cap was placed on a sample as a barrier to oxygen penetration before aging it and effectively the same aging behavior occurred. This rules out oxygen annealing during measurement as the mechanism for the decay. The other possibility is that oxygen combines with the Co during deposition in the vacuum chamber, although the level of the vacuum suggests that this should not be significant.

Nanoparticle Array in Matrix Material

We initially set out to produce nanoparticles of Co in a solid-state Sb matrix with growth formation through a Volmer-Weber growth mechanism. In an earlier study, we deposited samples at room temperature and gave significant time (5 min) after Co deposition to maximize nanoparticle growth. Every 5 multilayers the assembly was let cool for 30 minutes to maintain a deposition temperature of approximately room temperature.

We found in these samples magnetic signatures of 6-8 nm Co nanoparticles (Peak in ZFC, ZFC-FC remanence, 100K-200K blocking temperature, strong field dependence of peak, no waiting time effect), indicating that small Co particles were produced, and not perfect layers.

After aging, the nanoparticle signature disappeared. Low angle x-ray data showed no evidence of superlattice peaks corroborating the lack of ideal layering. Data on samples presented here were deposited on substrates held at 35° C. and 50° C. These samples showed a ferromagnetic signature as discussed above and no evidence of a blocking temperature (ZFCFC remnant, peak in ZFC magnetization). One distinct possibility considering the formation of nanoparticles is that single domain nanoparticles are forming at these raised deposition temperatures and these particles are responsible for the ferromagnetic signature.

However, there are other experimental approaches that can be used to form nanoparticle arrays within a matrix material.

Further Aspects, Including Applications and Devices

An aging sensor experiences a time and thermal environment similar to that of a monitored physical system of which it is part, or otherwise proximate. An advantage of nanoparticle-based aging sensors is that the characteristic aging parameters (such as time-temperature parameters, including a characteristic time) are readily controllable by adjusting e.g. the composition, size, shape, density, and/or configuration of the nanoparticles. This may be much simpler and/or versatile than trying to adjust the parameters of a bulk material or specific molecular compound.

Aging sensors allow improved safety, for example food may be okay if left outside the refrigerator, so long as the integrated aging is not above a monitored threshold. Typically expiry dates are based on time alone, and may wrongly indicate that food is not spoiled, even where the food has been mishandled and left out of the refrigerator. Indicators of temperature excursion may wrongly show that the food is spoiled even if the room temperature exposure is relatively short. The improved approach of the present invention allows the combination of time and temperature exposure to be more accurately monitored, giving a more accurate reading of whether food or other product has expired.

Example aging sensors include a solid-state structure that can be used to mimic, and hence determine, the aging properties of products, systems, and materials such as food items including dairy products, medical supplies, medical monitoring, chemicals (e.g. volatile chemicals), pathogen (e.g. bacterial) growth, electronic circuits such as semiconductor devices, mechanical components, structural components, materials, and the like. In some examples, the faster aging of hotter items can be monitored and determined using the electrical resistance and/or magnetization of a solid-state device. Other parameters, such as thermal resistance, specific heat, etc. may also be monitored. A distinct change in one or more parameters may be observed representing aging of the item of interest.

Example solid-state structures include nanoparticles and a matrix material. The nanoparticles may be magnetic nanoparticles, in particular ferromagnetic particles. Ferromagnetic nanoparticles may consist essentially of, or otherwise include one or more of the following: cobalt (Co), nickel (Ni), iron (Fe), manganese (Mn), or ferromagnetic rare earth material. Magnetic and electrical resistance may fall due to a variety of processes, such as nanoparticle melting, thermal demagnetization, etc. In some examples, magnetic nanoparticles may be formed in a magnetic multilayer device, for example a device including semimetal layers.

In some examples, magnetic and resistive properties of the structure are modified by the melting or other change in the form or state of the nanoparticles. For examples, the nanoparticles may initially be electrically isolated from each other, then melt into each other to provide a lower conductivity path through a matrix material. In such examples, the nanoparticles preferably have an electrical conductivity much greater than a surrounding or adjacent matrix material, for example one or more orders of magnitude greater. The structure may be used to monitor aging in the form of time-temperature combinations, or in some examples may be used to detect excursions above a certain threshold temperature.

Examples of the present invention include apparatus configured to provide a signal after a certain degree of aging has occurred. Aging in this context may correlate with the passage of time combined with one or more other parameters, such as temperature. For example, aging may relate to a time-temperature integration or other temperature modified time period. Aging may be related to an integration or other mathematical combination of a temperature excess beyond a threshold temperature and time, or other combination of physical parameter(s) and time.

An apparatus may include an electrical circuit responsive to a change in magnetization, resistance, or other parameter sensitive to the aging process. For example, an electronic circuit may be in electrical communication with a structure according to an example of the present invention and provide an electrical signal responsive to detected aging. In other examples, the electronic circuit may communicate with a transponder circuit including the structure, for example using capacitive or inductive RFID approaches. For example, a hand-held scanner may be used to interrogate the status of aging sensors on milk or other item.

An electronic circuit may provide a warning light, sound, or vibration in response to a detected degree of aging. An electronic display may be used to give a message. The change in conductivity in the structure may be used as a switch, and in some cases may be used as a fuse.

Aging may also be responsive to other conditions, such as pressure, humidity, presence of chemicals (such as oxidising agents), and the like. Some examples of the invention include devices responsive to such parameters. For example, external pressure or other mechanical force effects may induce reorientation, alignment, shape modification, and/or combination of nanoparticles, leading to a change in magnetic properties and/or resistance. For example, stretching of a component may be detected as nanoparticles are brought into contact with each other. Humidity may also influence the aging properties, and this may be detected in combination with time and/or temperature effects.

Examples of the present invention can be used to monitor a variety of systems or products, such as physical or chemical systems and a variety of commercial products. A solid-state structure, such as those described herein, may be included within the system (for example included within a system component), attached to a system component, or otherwise be exposed to similar conditions as the monitored system.

Monitored products may include food products, in particular perishable food products such as milk, other dairy products, meat, and the like. Aging may be monitored after packaging. In some cases, food processing may be monitored, e.g. to determine if a food product has been exposed to an excessive (or insufficient) combination of temperature and time during processing. This may help reduce the loss of nutrients during processing, or may be used to ensure sufficient sterilization.

Other monitored items may include medical supplies (such as pharmaceuticals), chemicals subject to aging degradation, and the like.

Other monitored items (such as physical systems) may include buildings, bridges, roads, other infrastructure, vehicles such as aircraft, and the like. For example, excessive forces in bridges or other dangerous excursions within component operating parameters may be detected, for example through an effect on the nanoparticles, such as local heating.

In some examples, a device may use a reversible effect, and may be reset e.g. using poling magnetic fields to restore ferromagnetic behavior of the nanoparticles. In some examples, the aging response may be non-reversible, in a single use device. The aging sensors may be cheap enough to be disposable, for example formed as a patch on a product to be monitored.

In some examples, the nanostructure, such as nanoparticles, have distinct shape anisotropy, having a dimension in one direction appreciably greater than dimension(s) in one or more orthogonal directions. The shape anisotropy, in the form of dimension ratios, may be greater than 2, for example greater than 5. The nanoparticles may be disks, flakes, rods, nanowires, and the like.

In some examples, the nanoparticles may be small enough to enhance melting under conditions of interest. For example, the nanoparticles may have a dimension (such as a diameter or equivalent thereof) in the range 0.1-10 nm, such as 0.5-5 nm, e.g. 1-2 nm. All ranges herein are inclusive, and in some examples may be approximate.

In some examples, the matrix material may be a semimetal or semiconductor such as arsenic (As), antimony (Sb), bismuth (Bi), tin (Sn), and the like, other semimetal, or combination or compound thereof. The nanostructure material may wet a matrix material surface on which it is deposited, facilitating the formation of flake-like nanoparticles that are much wider than they are thick.

In some examples, the matrix material may be a metal, preferably having an electrical conductivity appreciably less than that of the nanoparticle material. For example, a device may comprise magnetic nanoparticles and a relatively high resistance non-magnetic metal. Spin discontinuities at the nanoparticle interfaces increases the conductivity of the device. However, as nanoparticles either demagnetize or fuse together, the conductivity of the electrical path is reduced. This may be detected, and the degree of resistance (or magnetization) reduction can be used as an estimate of system aging.

In some examples, the nanostructures may be non-magnetic, and the matrix material may be a semimetal or relatively high resistivity metal. For example, copper, gold, silver etc. nanostructures may be formed in a tin, antimony etc. matrix. As the low resistivity nanoparticles fuse together, a lower conductivity path is formed which may then be electrically detected.

In some examples, the matrix material may be a semiconductor, e.g. with band discontinuities at the nanoparticle-matrix boundaries providing an impediment to electron or hole transport. In some examples, the matrix material may be or include a metalloid, such as boron, germanium, silicon, arsenic, antimony, or tellurium. In some examples, the matrix material may be a polymer and/or a flexible material, e.g. that may be conformed to a surface, stretched, etc.

The structure may be a multilayer structure, for example including one or more matrix material layers alternating with one or more nanoparticle layers. In some examples, nanoparticles may be dispersed through a matrix material, e.g. in the form of a composite.

Patents, patent applications, or publications mentioned in this specification are incorporated herein by reference to the same extent as if each individual document was specifically and individually indicated to be incorporated by reference. In particular, U.S. Provisional Application 61/476,044, filed Apr. 15, 2011, is incorporated herein by reference.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art.

Having described our invention, I claim:

1. A method of monitoring aging of an item, the method comprising:
    locating a solid-state structure proximate the item, the solid-state structure and item being subjected to a combination of time and ambient temperature, the solid-state structure including ferromagnetic nanoparticles of a first material distributed in a matrix material between a pair of electrodes, the matrix material being a semimetal or a semiconductor and magnetic interactions between neighboring nanoparticles resulting in temperature and time dependent electrical resistance and magnetization of the solid-state structure,
    measuring a physical parameter of the solid-state structure using the pair of electrodes, the physical parameter being an electrical resistance or a magnetization;
    determining a change in the physical parameter relative to an initial state of the solid-state structure, the change in the physical parameter being due to morphological changes of the nanostructures caused by the combination of time and ambient temperature; and
    determining the aging caused by the combination of time and ambient temperature of the item from the change in the physical parameter of the solid-state structure.

2. The method of claim 1, the morphological changes including melting of the nanoparticles, the melting of the nanoparticles facilitated by the magnetic interactions between the neighboring nanoparticles.

3. The method of claim 2, the melting of the nanoparticles forming nanowires of the first material through the matrix material.

4. The method of claim 3, the physical parameter being an electrical resistance,
    wherein measuring a physical parameter of the solid-state structure includes determining an electrical resistance between electrodes on the solid-state structure,
    the first material having an electrical conductivity greater than the matrix material,
    the electrical resistance falling as the item ages due to the formation of the nanowires of the first material.

5. The method of claim 1, the matrix material being a non-ferromagnetic material.

6. The method of claim 5, the ferromagnetic nanoparticles being cobalt, iron, manganese, nickel, or a ferromagnetic rare earth metal.

7. The method of claim 1, the physical parameter being magnetization, the magnetization falling as the item ages.

8. The method of claim 1, the physical parameter being electrical resistance, the electrical resistance decreasing as the item ages.

9. The method of claim 1, the matrix material being arsenic, antimony, tin, or bismuth.

10. The method of claim 1, the item being a food item, medical item, a chemical compound, or a mechanical component.

11. The method of claim 1, the change in the physical parameter being a function of an elapsed time from the initial state,
    the change in the physical parameter further being a function of temperature variations within the elapsed time,
    the change in the physical parameter further being a function of temperature of the solid-state structure.

12. An apparatus for monitoring a degree of aging of an item, the apparatus comprising:
    a solid-state structure including ferromagnetic nanoparticles of a first material distributed in a matrix material between a pair of electrodes, the matrix material being a semimetal or a semiconductor and magnetic interactions between neighboring nanoparticles resulting in temperature and time dependent electrical resistance and magnetization of the solid-state structure,
    the solid-state structure having a physical parameter, the physical parameter being an electrical resistance or a magnetization,
    the solid-state structure having an initial state having an initial value of the physical parameter and an aged state caused by a combination of time and ambient temperature and having an aged value of the physical parameter,
    the physical parameter changing from the initial value to the aged value due to morphological changes of the nanostructures caused by the combination of time and ambient temperature.

13. The apparatus of claim 12, the nanoparticles being metal nanoparticles.

14. The apparatus of claim 13, the solid-state structure being a multilayer structure, including a layer of nanoparticles formed between layers of the matrix material,
    the nanoparticles being nanoflakes in the initial state,
    the nanoparticles including nanowires in the final state, the nanowires being formed from melting together of adjacent nanoflakes.

15. An apparatus for monitoring a degree of aging of an item, the apparatus comprising:
    a solid-state structure including nanoparticles of a ferromagnetic material distributed through a matrix material, the matrix material being a non-ferromagnetic semimetal or a semiconductor and magnetic interactions between neighboring nanoparticles resulting in temperature and time dependent electrical resistance and magnetization of the solid-state structure;
    a first electrode, in electrical contact with the solid-state structure; and
    a second electrode, in electrical contact with the solid-state structure,
    the matrix material having an electrical resistivity at least one order of magnitude greater than the ferromagnetic material at an operating temperature of the apparatus,
    the solid-state structure having an initial state having an initial electrical resistance and an aged state caused by a combination of time and ambient temperature and having an aged electrical resistance, the electrical resistance between the first and second electrodes decreasing as a function of time and ambient temperature during a transition from the initial state to the aged state.

16. The apparatus of claim 15, the electrical resistance between the first and second electrodes decreasing due to morphological changes in the nanoparticles, the morphological changes including melting of the nanoparticles.

17. The apparatus of claim 15, the physical property of the apparatus in the aged state being reversible to the initial state by application of an external magnetic field.

18. The apparatus of claim 15, the solid-state structure being a multilayer structure including at least one layer of the nanoparticles between layers of the matrix material.

19. The apparatus of claim 18, the electrodes being configured to determine electrical resistivity parallel to layers of the multilayer structure.

20. The apparatus of claim 18, the electrodes being configured to determine electrical resistivity perpendicular to layers of the multilayer structure.

* * * * *